United States Patent [19]

Tracy

[11] 4,160,323
[45] Jul. 10, 1979

[54] PORTABLE DENTAL CABINET

[76] Inventor: Ronald J. Tracy, 2603 E. Main St., Sumner, Wash. 98390

[21] Appl. No.: 808,198

[22] Filed: Jun. 20, 1977

[51] Int. Cl.² .............................................. A61C 19/00
[52] U.S. Cl. ........................................ 32/22; 312/209
[58] Field of Search .................... 32/22; 312/209, 277; 366/602

[56] References Cited

U.S. PATENT DOCUMENTS

| | | | |
|---|---|---|---|
| 612,373 | 10/1898 | Allison | 312/209 |
| 2,524,523 | 10/1950 | Greenberg | 366/602 |
| 3,081,542 | 3/1963 | Sherfey | 32/22 |
| 3,089,741 | 5/1963 | Burton | 312/209 |
| 3,229,368 | 1/1966 | Tocchini | 32/22 |
| 3,718,972 | 3/1973 | Fox et al. | 32/22 |
| 3,734,122 | 5/1973 | Cousins | 32/22 |

FOREIGN PATENT DOCUMENTS 2306676  11/1976  France ......................... 32/22

*Primary Examiner*—Louis G. Mancene
*Assistant Examiner*—John J. Wilson
*Attorney, Agent, or Firm*—Trexler, Wolters, Bushnell & Fosse, Ltd.

[57] ABSTRACT

A mobile dental unit is disclosed which provides physical support for dental operations during a long period of time when the operations are conducted in remote or out-of-office areas. A wheeled cabinet defines a lower compartment containing a source of compressed air, a vacuum chamber and a vacuum pump. The upper compartment contains a storage space, a pressurizable water reservoir, and an amalgamator. The source of compressed air illustrated here is a tank of the variety offered for use in self-contained underwater breathing apparatus. This source tank provides air for direct use in dental operations and also operates the pneumatic drives of dental handpieces. A patient support structure can be associated with the unit to permit an infirm patient to be treated in a supine position.

16 Claims, 12 Drawing Figures

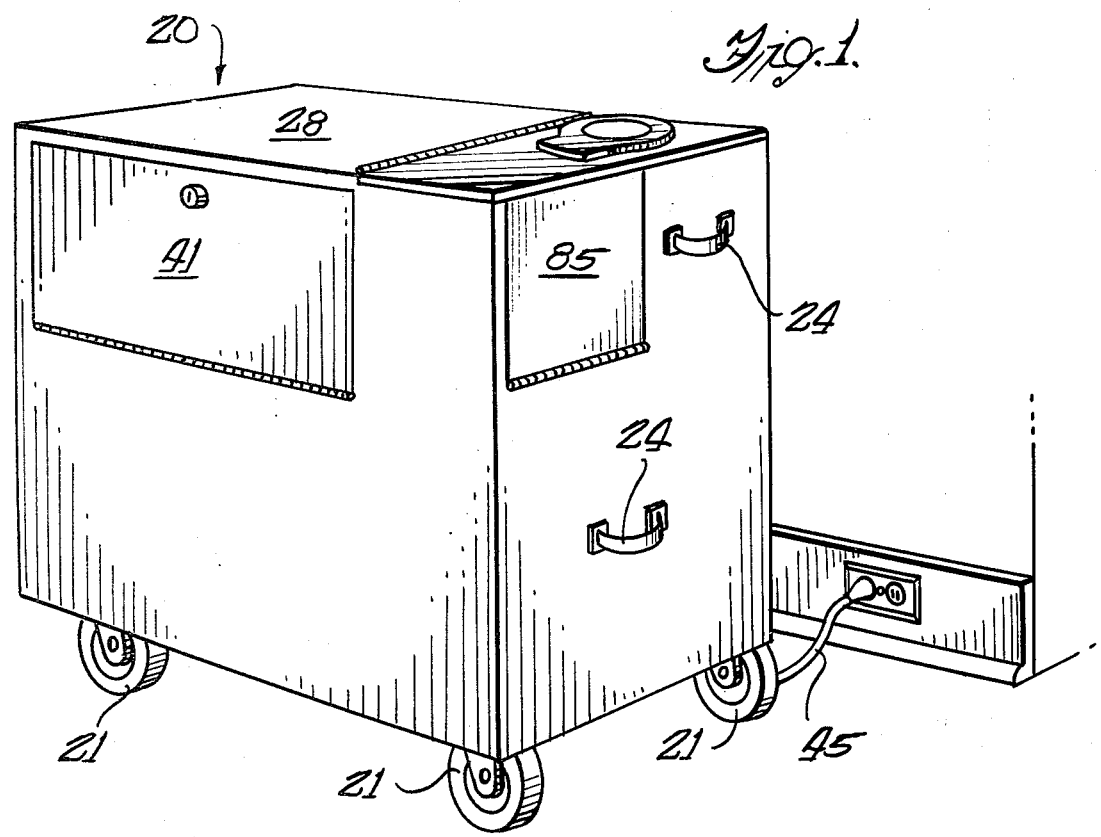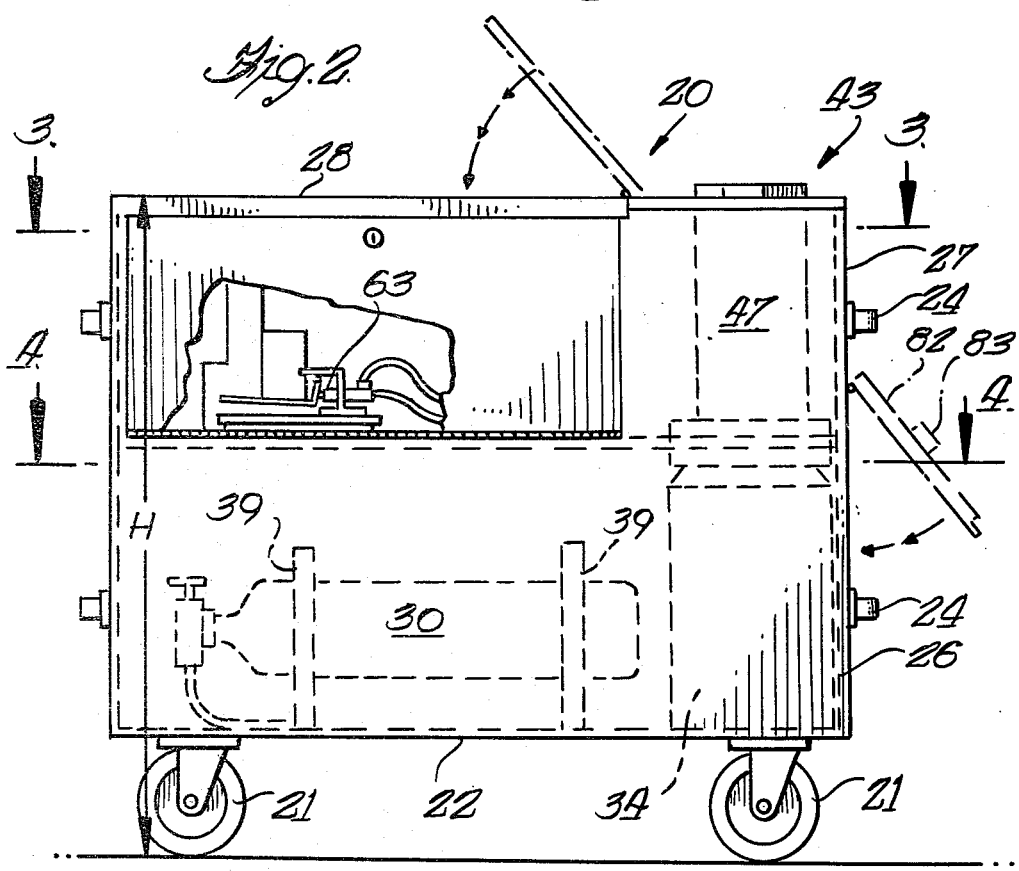

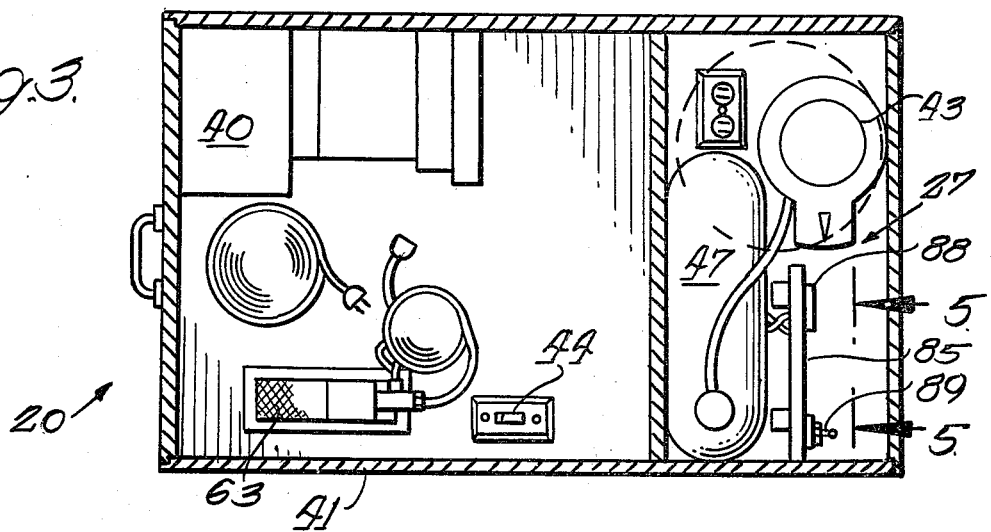
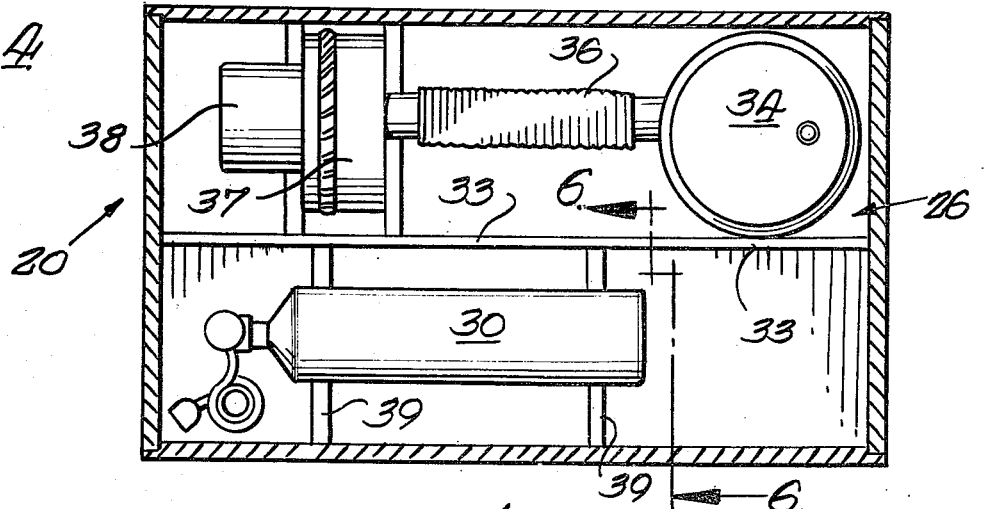
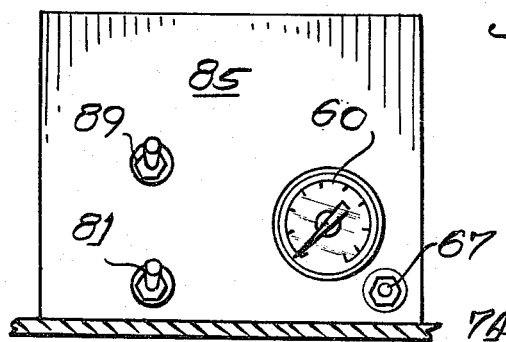
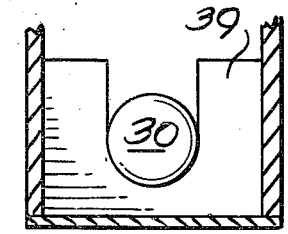
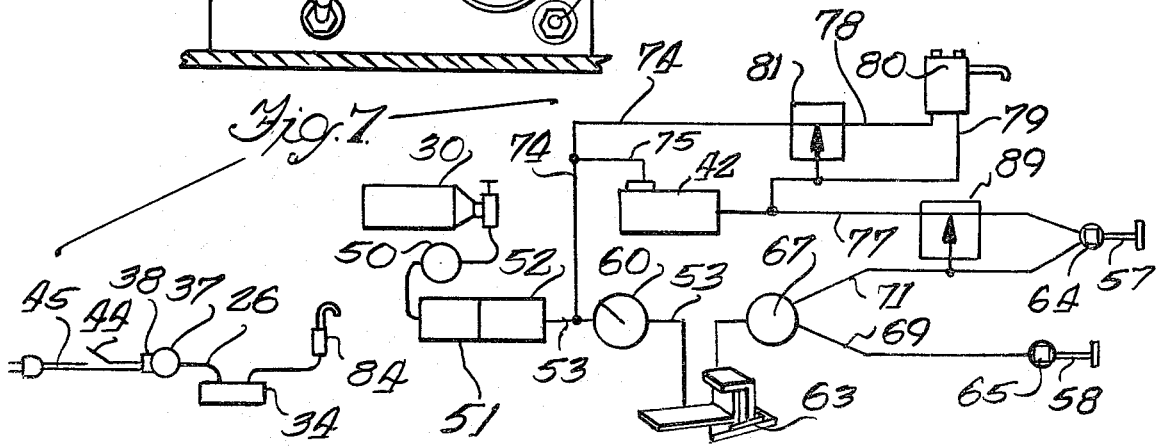

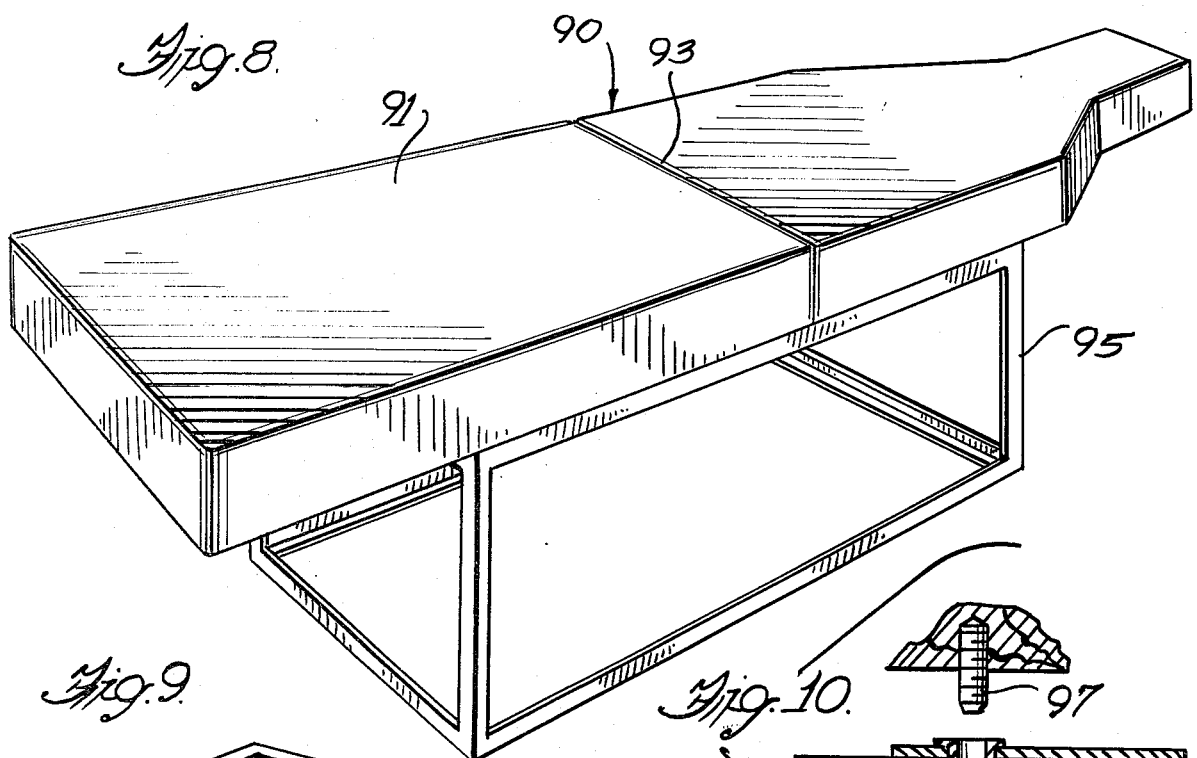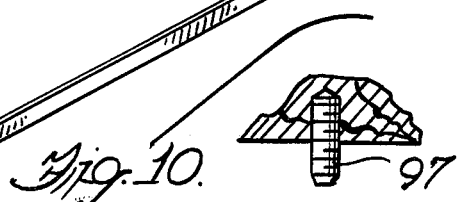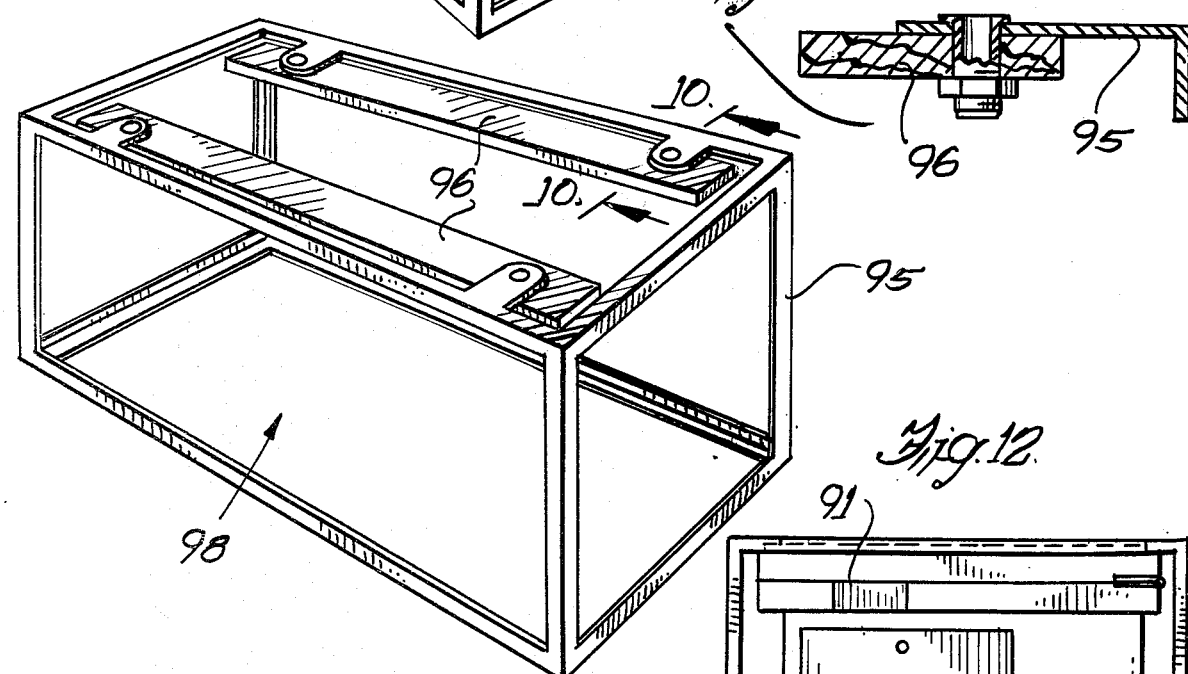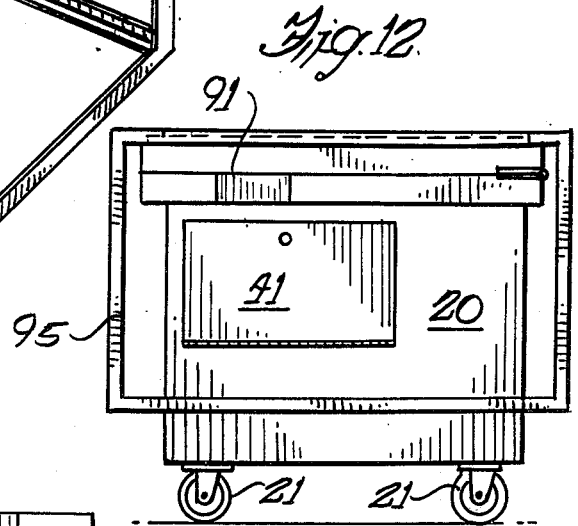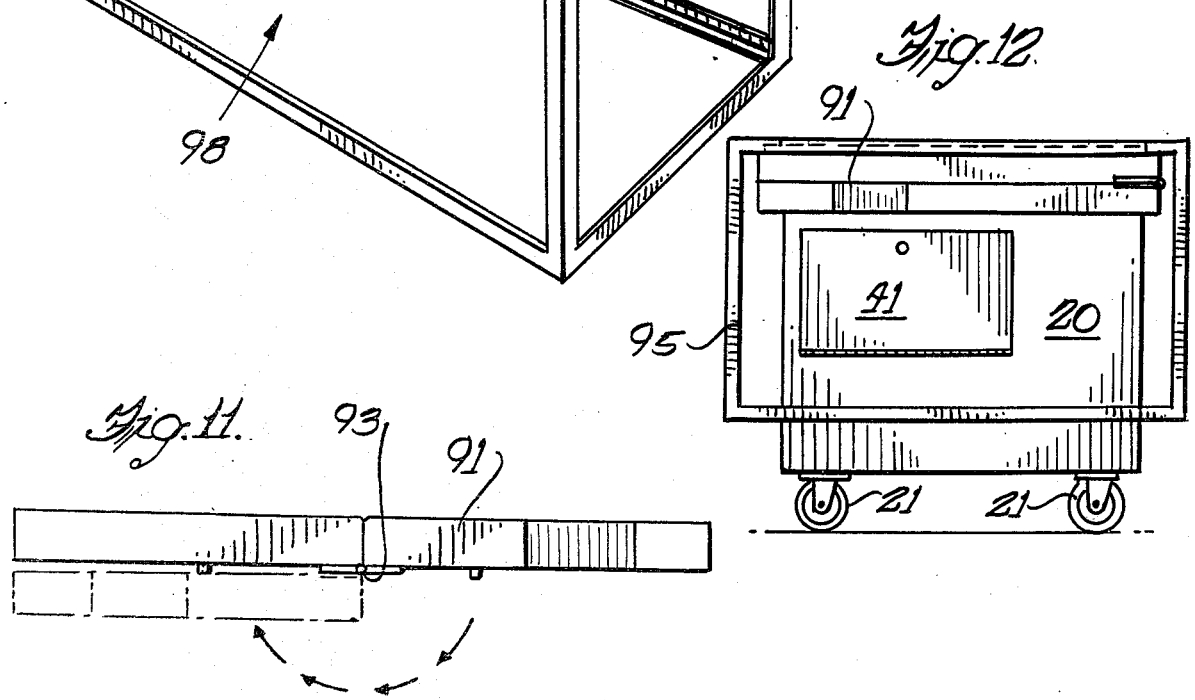

4,160,323

PORTABLE DENTAL CABINET

BACKGROUND OF THE INVENTION

This invention relates generally to dental operatories for out-of-office use, and more particularly concerns a mobile dental operatory especially constructed for use in relatively remote locations, and for use with incapacitated patients.

With increasing public acceptance of the idea of adequate dental care—of at least a basic or minimal nature—there has arisen a corresponding demand for dental care by persons who are not able to come to a dentist's office. These persons may be sick, or old and infirm, or otherwise incapacitated. Additionally, some persons live or work in areas which are so remote as to make travel to a dentist's office almost impossible. To such persons, dental care must be brought.

Dental operatories which can be moved from place to place are disclosed in U.S. Pat. Nos. 3,077,665 to Saltzman, 3,081,542 to Sherfey, and 3,111,759 to Shackelford, among others. An examination of these patents shows, however, that the disclosed units are not especially adapted for rugged use, and are not capable of supporting dental operatory work for extended periods of time away from an office or other permanent base. The disclosed units are not, for example, especially adapted for easy transportation and satisfactory use in remote geographical regions such as lumbering camps, fishing villages, or other areas. Nor are these units especially adapted to withstand the rigors of a great number of trips in and about even urban areas. No consideration has been given to years of heavy use and transportation from a dentist's base of operations to convelescent homes, homes for aged persons, and the like. Still further, such units do not lend themselves readily to extended periods of use without resupply. For example, such units are not especially adapted to provide three to five days of dental care operations without replenishment.

It is accordingly the general object of the present invention to provide a rugged mobile dental operatory unit which will meet the foregoing requirements. Alternately put, it is an object of this invention to provide a mobile dental operatory unit which can be quickly and easily secured in a small truck, van, automobile or like conveyance for relatively long trips to isolated areas, which can provide support for several days of dental work, and which will withstand years of rugged use.

Another object is to provide such a unit which can be easily moved over all types of ground surfaces.

Still another object is to provide a dental operatory unit which can be used in remote, isolated field treatment situations with minimum setup time.

A further object is to provide such a unit which can be easily used with minimum effort by the dentist in treating either reclining or supine patients who are feeble or otherwise prevented from sitting erect.

A yet further object is to provide such a unit having a workspace located at a height which is handy to either a sitting or a standing dentist.

Other objects and advantages of the invention will become apparent upon reading the following detailed description and upon reference to the drawings. Throughout the drawings, like reference numerals refer to like parts.

BRIEF DESCRIPTION OF THE DRAWINGS

FIG. 1 is a perspective view showing the novel dental operatory unit of the present invention as it appears in its general aspect;

FIG. 2 is a side elevational view of the unit;

FIG. 3 is a sectional view taken substantially in the plane of line 3—3 in FIG. 2;

FIG. 4 is a sectional view taken substantially in the plane of line 4—4 in FIG. 2;

FIG. 5 is a sectional view taken substantially in the plane of line 5—5 in FIG. 3;

FIG. 6 is a sectional view taken substantially in the planes of lines 6—6 in FIG. 4;

FIG. 7 is a schematic diagram illustrating the arrangements and interrelationships of major unit components;

FIG. 8 is a perspective view of a portable couch or patient support structure for use with the mobile dental operatory;

FIG. 9 is a perspective view of the patient support frame;

FIG. 10 is a sectional view taken substantially in the plane of line 10—10 in FIG. 9;

FIG. 11 is a side elevational view illustrating a portion of the support couch in its folded and, alternatively, in its unfolded positions; and FIG. 12 is an elevational view of the mobile dental unit and associated patient support as they appear when ready for travel.

DETAILED DESCRIPTION

While the invention will be described in connection with a preferred embodiment, it will be understood that it is not intended to limit the invention to this embodiment. On the contrary, it is intended to cover all alternatives, modifications and equivalents as may be included within the spirit and scope of the invention as defined by the appended claims.

Turning first to FIGS. 1-4, there is shown a mobile dental unit 20, here manufactured of exterior grade plywood and covered with plastic laminate for ease of cleaning and durability. To permit the unit 20 to be easily moved over all types of ground and floors, four large-diameter casters 21 are mounted on the unit bottom 22. When the caster wheels are selected so as to have a diameter on the order of 5 inches, the unit can be easily pulled about over even rough surfaces by handles 24 secured to the unit 20 itself.

For easy maintenance and use, the unit 20 is divided into a lower compartment 26 and an upper compartment 27. A planer top 28 covers the upper compartment 27 and provides a convenient horizontal surface upon which to lay out dental instruments and related materials for dental operations. In accordance with one aspect of the invention, the compartments 26 and 27 and casters 21 together provide an overall unit height H (FIG. 2) sufficient to locate the upper compartment top 28 conveniently for use by the dental operator when he is in either a standing or a sitting position. This permits the unit to be conveniently used by the dental operator when he is treating a patient who is confined to a bed, or in a supine position upon the patient support 90 described below, or in a sitting position which may be assumed by more able patients. It will be understood that if the demands of transportation dictate, the unit 20 can be constructed so as to make separable the upper and lower compartments 26 and 27.

In accordance with another aspect of the invention, the unit 20 has a low center of gravity so as to discourage tipping when the unit is being moved over door sills or from place to place. To this end, the lower compartment 26 contains a source of compressed air 30, and, on an opposite side of a lower compartment partition 33, a vacuum chamber 34 is connected, by a vacuum-drawing line 36, to a vacuum pump 37 which is operated by an electric motor 38. When the vacuum chamber 34 is connected to an aspirator as described below, the vacuum chamber 34 collects liquid and solid waste, and retains the material within the chamber 34, but air and other gases can be drawn from the vacuum chamber through the hose-like vacuum conduit 36 by the vacuum pump 37. Preferably, this vacuum pump 37 is capable of drawing on the order of 100 cubic feet per minute of free air at a vacuum or negative pressure of about five inches of mercury. Gas and air drawn by the pump 37 from the chamber 34 are exhausted through four holes (not shown) in the unit base. Thus, bacteria and the like air-borne wastes are not retained within the cabinet, nor are they directed to positions where they might be able to find their way into the compressed air system portions of the unit 20.

In accordance with yet another aspect of the invention, the source 30 of compressed air cannot be contaminated by bacteria, germs, or other air-borne materials, requires no external power, is lighter in weight and less expensive than the ordinary air compressor, and yet provides sufficient compressed air for a day or more of dental operations. To this end, the source of compressed air here takes the form of a pressurizable air containing tank. Unit manufacturing expense can be lowered by selecting this pressurizable tank 30 to be of the type offered for use with self-contained underwater breathing apparatus. These scuba tanks can, for example, be pressurized to contain approximately 72 free cubic feet of air at approximately 2250 psig. The tank itself is securely carried in saddles 39.

Within the upper compartment 27, there is a storage space 40 which can be used to retain dental operation implements, gauzes, raw materials or the like. Access to the storage space 40 is provided by a door 41. A pressurizable water reservoir 42 here takes the form of a plastic water bottle such as that found in automobile windshield washer systems, and is capable of carrying sufficient water for approximately three days of dental operations.

Adjacent this water reservoir 42 is an amalgamator 43. Preferably, this amalgamator 43 is of the McShirley Jr. type, and permits the convenient preparation of dental filling amalgam material while other portions of various dental operations are being carried out.

An off-on switch 44, conveniently located near the door 41, provides electric power to the vacuum pump motor 38 via a line cord 45 (FIG. 1). As explained below, this power is the only externally originating power used, and if the vacuum feature of the unit 20 is not needed or can be dispensed with, the unit of the present invention is entirely self-supporting. Under these conditions, the unit 20 permits dental operation to be carried out for days on end in locations which are, quite literally, completely isolated.

In further accordance with this aspect of the invention, compressed air contained within the tank 30 is used not only directly in dental operations, but also indirectly to provide a source of motive power for various devices comprising parts of the dental unit. To this end, as shown in FIG. 7, air is passed from the tank 30 through a preliminary or first-stage depressurizing demand regulator 50, through a filter 51, and a second, adjustable demand regulator 52 to a first flexible pneumatic line 53. Conveniently, the first regulator 50 can be set to reduce the pressure of the air delivered from the tank 30 to approximately 60 psig, and to pass this air through a 5 mm filter 51 to insure pure air delivery through the patient. A second regulator 52 further reduces the air pressure to approximately 40 psig for delivery to downstream system units.

Actual oral work is accomplished by means of a high speed dental handpiece 57 or a slow speed handpiece 58. To operate these handpieces 57 and 58, the first flexible pneumatic conduit hose 53 is connected between the low pressure regulator 52, and the handpieces 57 and 58 through an appropriate pressure-monitoring gauge 60. A foot-pedal type control 63 can be used to adjust the air pressure delivered to the downstream pneumatic handpiece drives 64 and 65 and consequently regulate the operating speed of the handpieces 57 and 58. A selector 67 delivers air to an extension portion 69 of the first conduit 53 or, alternatively, to another portion 71 of the first conduit 53 for delivery to the handpiece 57.

A second pneumatic conduit 74, directly connected to the first conduit 53, delivers compressed air via a branch 75 to the pressurizable water reservoir 42. When the reservoir 42 is pressurized, a flexible water conduit 77 can deliver water to the handpiece 57, to permit a water cooling spray to be provided as the handpiece is used. Water is also delivered, via a branch line 79, to a syringe 80. The second flexible pneumatic conduit 74 is also connected to the syringe 80 by a third conduit 78 to permit a selector control 81 to deliver air, water, or an air-water mix to appropriate portions of the patient's mouth during operations.

When conducting dental operations, it is helpful to locate the syringe 80 and handpieces 57 and 58 for ready access by the operating dentist. To this end, the unit is provided with a fold down panel 82 as shown in FIG. 2, and on this panel 82 can be mounted a bracket array 83 for holding the syringe handpieces and any other desired items.

By reference to FIG. 7, it will be noted that an aspirator 84 can be connected to the vacuum chamber 34, and, consequently, indirectly connected to the vacuum pump 37. However, there is no interconnection from the vacuum system to the compressed air system and other portions of the unit. In this way, the unit positively prohibits entry of bacteria, dirt, or other corruption into those portions of the system which deliver fluids to the patient during the dental operation.

The handpieces 57 and 58 can be controlled from a control panel 85 as shown in FIG. 5. The pneumatic conduits 69 or 71 can be plugged into the selector receptacle 67, and the line air pressure monitored through the gauge 60. An upper switch 89, when set in the illustrated up position, provides a high speed to the handpiece 57 and, in its down position, provides a low speed operation. The bottom switch 81 permits or halts water flow to the syringe 80 as explained above.

It is another feature of the invention that a patient support device 90 can be offered for use with the unit 20, and the support 90 will comfortably accommodate even infirm patients in a supine position. This patient support device 90 here takes the form of a foldable patient couch cushion 91 which can be conveniently folded and unfolded about a bisecting hinge 93 as illustrated in FIGS. 8 and 11. The couch unit 91 itself is mounted atop a frame 95 which can be of a box-construction variety. Couch support members 96 permit pin-type connections 97 (FIG. 10) carried by the couch 91 to be inserted into the frame 95 to provide a rigid, comfortable, stable support 90. The bottom of the frame 95 provides a recess 98 sufficiently large to permit the frame 95 to be placed in a surrounding, overlying position on and around the mobile unit 20 as illustrated in FIG. 12 for easy, convenient, compact movement and storage.

The invention is claimed as follows:

1. A compact, lightweight, mobile dental unit, having a low center of gravity, comprising a wheeled cabinet, defining a lower compartment and a planar-top upper compartment, the cabinet compartments having a stacked height sufficient to locate the upper compartment top at a height convenient for dental operations use by either a standing or sitting dentist, the lower compartment containing a source of compressed air comprising a horizontally disposed tank of the type offered for use with self-contained underwater breathing apparatus, a vacuum chamber, and a vacuum pump connected to the vacuum chamber so as to draw gas from the vacuum chamber while permitting liquids and solids to be retained in the vacuum chamber, the upper compartment containing a storage space, a pressurizable water reservoir, and an amalgamator for preparing dental cement, the unit further comprising a first dental handpiece, a first dental handpiece pneumatic drive, first flexible pneumatic conduit means leading from the source of compressed air to the first dental handpiece pneumatic drive, first flexible water conduit means leading from the pressurizable water reservoir to the dental handpiece the unit further comprising a foldable patient support for supporting the patient in a supine position, and support frame means removably mounted on said cabinet for carrying the foldable patient support and for supporting the patient at a convenient operating elevation, and at a location spaced apart, if desired, from the cabinet, said frame means defining a recess sufficiently large to permit the frame means to be placed in a surrounding, overlying position on and around the wheeled mobile dental unit cabinet for transporting the cabinet and patient support, and to permit the frame means and patient support to be removed from contact with the wheeled cabinet for patient support use.

2. A mobile dental unit according to claim 1 wherein said source of compressed air includes a pressurizable air-containing tank.

3. A mobile dental unit according to claim 2 wherein said pressurizable tank is a tank of the type offered for use with self-contained underwater breathing apparatus, and is, when contained within the mobile dental unit, unconnected to any other delivery source of compressed air.

4. A mobile dental unit according to claim 3 wherein said compressed air tank is capable of retaining approximately 72 free cubic feet of air compressed to a pressure of substantially 2250 psig.

5. A mobile dental unit according to claim 2 wherein said unit includes a regulator mechanism connected to the pressurizable tank and to the flexible pneumatic conduit means for reducing the pressure of the air leaving the tank to approximately 60 psig.

6. A mobile dental unit according to claim 1 including means separating said vacuum pump from said source of compressed air, the separating means positively inhibiting gases exhausted from said vacuum pump from entering the pressurizable tank, flexible pneumatic conduit means, and pneumatic handpiece drive.

7. A mobile dental unit according to claim 1 wherein said vacuum pump is capable of drawing up to substantially 100 cubic feet of air per minute at a vacuum of substantially two inches of mercury vacuum.

8. A mobile dental unit according to claim 1 further comprising second flexible pneumatic conduit means for leading compressed air to the pressurizable water reservoir.

9. A mobile dental unit according to claim 8 wherein said second flexible pneumatic conduit means is connected to said first flexible pneumatic conduit means so as to lead compressed air directly from the first flexible pneumatic conduit means to the pressurizable water reservoir.

10. A mobile dental unit according to claim 1 including a fold-down panel formed in and on the wheeled cabinet, and bracket means carried on the fold-down panel for temporarily and removably mounting any dental handpieces.

11. A mobile dental unit according to claim 1 including a syringe, and a third flexible pneumatic conduit means for leading compressed air to the syringe.

12. A mobile dental unit according to claim 11 wherein said third flexible pneumatic conduit means is connected directly to said second flexible pneumatic conduit means so as to lead compressed air directly from the second flexible conduit means to the syringe via the third flexible conduit means.

13. A mobile dental unit according to claim 11 including second flexible water conduit means for leading pressurized water to the syringe.

14. A mobile dental unit according to claim 13 wherein said second flexible water conduit means is connected directly to said first flexible water conduit means and to the syringes so as to lead pressurized water to the syringe directly from the second flexible water conduit means.

15. A mobile dental unit according to claim 1 including foot control means interposed in the first flexible pneumatic conduit means between the source of compressed air and the dental handpiece pneumatic drive, whereby to control the drive action of the pneumatic drive.

16. A mobile dental unit according to claim 1 including an aspirator, and vacuum conduit means connecting the aspirator to said vacuum chamber independently of said compressed air source and said flexible pneumatic conduit means.

* * * * *